United States Patent
Kaldestad

[11] Patent Number: 5,947,730
[45] Date of Patent: Sep. 7, 1999

[54] INCREASED TAPER SEGMENTAL ROTARY FILES

[75] Inventor: Roy N. Kaldestad, San Antonio, Tex.

[73] Assignee: Board of Regents, The University of Texas System, Austin, Tex.

[21] Appl. No.: 08/962,493

[22] Filed: Oct. 31, 1997

[51] Int. Cl.[6] ........................................... A61C 5/02
[52] U.S. Cl. ........................................... 433/102
[58] Field of Search ............................... 433/102

[56] References Cited

U.S. PATENT DOCUMENTS

| | | | |
|---|---|---|---|
| 4,332,561 | 6/1982 | McSpadden | 433/102 |
| 4,353,698 | 10/1982 | McSpadden | 433/164 |
| 4,457,710 | 7/1984 | McSpadden | 433/81 |
| 4,708,651 | 11/1987 | Buchanan | 433/157 |
| 4,734,035 | 3/1988 | Cheng et al. | 433/102 |
| 4,836,780 | 6/1989 | Buchanan | 433/102 |
| 4,850,867 | 7/1989 | Senia et al. | 433/102 |
| 4,904,185 | 2/1990 | McSpadden | 433/164 |
| 4,934,934 | 6/1990 | Arpaio, Jr. et al. | 433/102 |
| 4,971,556 | 11/1990 | Ritano | 433/102 |
| 5,035,617 | 7/1991 | McSpadden | 433/102 |
| 5,104,316 | 4/1992 | McSpadden | 433/102 |
| 5,219,284 | 6/1993 | Velvart et al. | 433/102 |
| 5,257,934 | 11/1993 | Cossellu | 433/102 |
| 5,275,562 | 1/1994 | McSpadden | 433/224 |
| 5,498,158 | 3/1996 | Wong | 433/102 |
| 5,503,554 | 4/1996 | Schoeffel | 433/102 |
| 5,605,460 | 2/1997 | Heath et al. | 433/224 |
| 5,752,825 | 5/1998 | Buchanan | 433/102 |

OTHER PUBLICATIONS

Extraordinary Quantec by Tycom™ Endodontic Instrumentation, 17802 Fitch Irvine, CA 92614, (800) 288–6484 (publication date unknown).

Introducing ProFile® .04 Taper™ Series 29® Rotary Instruments, The New Revolution in Instrumentation, Tulsa Dental Products, 5001 E. 68th Street, Fifth Floor, Tulsa, Oklahoma USA 74136, Jan. 1995.

*Primary Examiner*—John J. Wilson
*Attorney, Agent, or Firm*—Arnold, White & Durkee

[57] ABSTRACT

The present invention comprises an endodontic instrument for preparing root canals in which the cutting surface has an increased taper greater than about 0.06 mm/mm. In the present invention, a plurality of files may be used in which each succeeding file has a minimum diameter substantially equal to the maximum diameter of the preceding file. By using the files of the present invention, a root canal may be prepared using a minimum number of files.

31 Claims, 2 Drawing Sheets

INCREASED TAPER SEGMENTAL ROTARY FILES

FIELD OF THE INVENTION

The present invention relates to instruments used for endodontic, or root canal, therapy. More specifically, the present invention relates to instruments used to prepare the root canal for filling.

BACKGROUND OF THE INVENTION

Endodontic therapy is used to save a patient's tooth when the soft tissue (pulp) in the tooth center becomes infected or nonvital. Steps in such therapy include opening the tooth, removing the pulp, cleaning, shaping, and smoothing the dentinal walls, and filling the tooth with a desired material, such as gutta percha.

In preparing a root canal for filling, it is important to consider the desired shape of the prepared root canal. The ideal root canal preparation is a continuously tapering funnel shape from the root apex to the orifice of the canal, with the narrowest dimension at the apex and the widest dimension at the orifice. Ideally, the prepared root canal should be the same shape as the original canal, except larger. Historically, the canal was prepared with files fabricated of stainless steel having a standardized taper of about 0.02 mm/mm. With these instruments, the taper of the funnel shape was created by the so-called "step back technique," involving taking progressively larger diameter instruments into the canal at serially shorter lengths (typically either 0.5 or 1.0 mm for each step back). This technique is sensitive, as well as tedious and fatiguing. A further drawback of the step-back technique is that, while it does create a funnel shape, it is not a continuous funnel, as it leaves small steps in the canal walls. These steps make filling more difficult.

Within the last few years, various companies have marketed files, both hand and rotary files, made of nickel-titanium, which is a much more flexible material than stainless steel. The rotary instruments may be used in a slow-speed, high-torque handpiece, which allows for better centering of the canal preparation and less operator fatigue. Such nickel titanium tools still need to be used in a step-back fashion, however, because the instruments become too stiff and have a tendency to screw themselves into the tooth when the taper is increased beyond approximately a 0.06 mm/mm taper.

SUMMARY OF THE INVENTION

The present invention, in a broad aspect, comprises an endodontic instrument for preparing a root canal, including a cutting surface having a minimum diameter distal portion and a maximum diameter proximal portion, and a taper between about 0.067 mm/mm and about 0.133 mm/mm, and a neutral rake angle and a non-cutting tip located adjacent the minimum diameter distal portion. The non-cutting tip is used to prevent transportation of the canal. The endodontic instrument may include a shaft segment located adjacent to the maximum diameter proximal portion, and a shank located adjacent the shaft segment. In an exemplary embodiment, the shank may include markings or a stop to indicate varying lengths of the instrument. Further, in an exemplary embodiment, the cutting surface may be between about 1.5 mm and 10.0 mm in length.

The present invention also includes a set of endodontic instruments for preparing a root canal, including a plurality of files, each having a tapered cutting portion defined by a maximum diameter and a minimum diameter, and wherein the minimum diameter of a first file substantially equals the maximum diameter of a second file, and so on, for other files. In an exemplary embodiment, the plurality of succeeding tapered files are equally tapered, and each file may have a non-cutting tip with a substantially equal diameter. In exemplary embodiments, a set may include a first file having a minimum diameter of about 0.25 mm and a maximum diameter of about 0.45 mm; a second file having a minimum diameter of about 0.45 mm and a maximum diameter of about 0.65 mm; and a third file having a minimum diameter of about 0.65 mm. These files may have cutting portions between about 1 mm and about 10 mm in length.

The present invention also includes a set of endodontic instruments for preparing a root canal with a first tapered file having a first minimum diameter and a first maximum diameter and a taper ratio greater than about 0.06 mm/mm; and a second tapered file having a second minimum diameter and a second maximum diameter, where the second minimum diameter is substantially equal to said first maximum diameter. The set may also include a third tapered file having a third minimum diameter and a third maximum diameter, where the third minimum diameter is substantially equal to said second maximum diameter.

The present invention also includes a method of preparing a root canal for filling, comprising firstly filing to a cementodentinal junction using a first instrument having a taper ratio greater than about 0.06 mm/mm; secondly filing to a first point proximal of the cementodentinal junction using a second instrument having a taper ratio greater than about 0.06 mm/mm; and thirdly filing to a second point proximal of the first point using a third instrument having a taper ratio greater than about 0.06 mm/mm. All of the instruments may comprise substantially the same taper, or different tapers.

DESCRIPTION OF ILLUSTRATIVE EMBODIMENTS

The endodontic files of the present invention may be made from a variety of materials, including but not limited to, selected alloys. In an exemplary embodiment, the alloy may be a nickel titanium alloy. The files may be manufactured to be used in a rotary instrument, such as a slow speed, high-torque electric handpiece at a speed of between approximately 150 and 350 rpm. Alternately, the files may be used manually.

As discussed above, the files of the present invention may be used for endodontic treatment of human teeth to prepare the root canal in a continuous funnel shape. This shape is desirable, as a "stair-step" pattern can cause damage to and future failure of the root canal. Also, a smooth continuous taper allows for an easier placement of the filling material, and better adaptation of the filling material.

Figure 1:
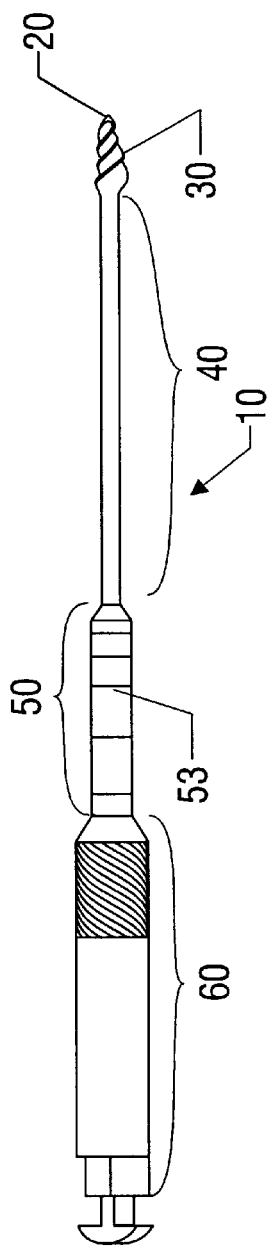
FIG. 1 is a side view of a most apical instrument according to the present invention.

As shown in FIG. 1, the files may include a non-cutting segment 20, a cutting portion 30, a shaft segment 40, a shank portion 50, and a latch attachment 60 for coupling to a rotary instrument (not shown). The cutting portion 30 may have flat outer edges 35, and a U-file design with radial lands (not shown) and a neutral rake angle (not shown). The non-cutting segment 20 may be a conical tip that, in an exemplary embodiment, has a taper angle of approximately 60°. The conical tip permits a smooth transition to the radial lands and prevents the instrument from transporting the canal.

One feature of the present invention is that by using an increased taper, otherwise called aggressive taper of the cutting segment as compared to prior art devices, fewer files are needed to prepare a root canal. The present invention provides files with cutting segments having a taper ratio between about 0.06 mm/mm (meaning a 0.06 mm increase in diameter per mm of length) and 0.15 mm/mm, and more preferably between about 0.067 mm/mm and about 0.133 mm/mm. In contrast, prior art files generally have taper ratios having a maximum of about 0.06 mm/mm.

Thus, by using the increased taper files of the present invention, it is possible to prepare a root canal using fewer files. Specifically, as few as three files are needed to successfully prepare a root canal using the equipment and methods of the present invention (it is to be understood, however, that more files may be used, if desired). In an exemplary embodiment, a set of three files may comprise a most apical instrument to be used first, a middle instrument to be next used, and a most coronal instrument to be used last. These three instruments may also be called a first instrument, a second instrument, and a third instrument, respectively.

The files of the present invention also permit a more desirable preparation of the root canal than prior art files. The files of the present invention may be used in sets (e.g., sets of three), with each of the files having the same taper ratio, but having different diameters and cutting lengths. By using files having the same taper ratio, a practitioner can prepare a root canal having a smooth, funnel shape. Such a smooth shape is preferred over a so-called stair-step pattern, which may result from using a set of prior art files each having a different taper ratio.

A set of files according to the present invention has another feature that aids in creation of a smooth shaped root canal. The minimum diameter of the cutting portion of a succeeding file (e.g., the second instrument) is substantially the same as (and preferably identical to) the maximum diameter of the cutting portion of the preceding file (e.g., the first instrument) of the set. Further, in an exemplary embodiment, all first instruments may have substantially the same minimum and maximum diameter of cutting portions, regardless of length and taper ratio of the instrument. Similarly, all second instruments and all third instruments may respectively have substantially the same minimum and maximum diameter of cutting portions. Thus, a practitioner may use a first instrument of one taper ratio, and second and/or third instruments of a different taper ratio, and still prepare a smooth, tapered root canal.

Instruments of various lengths, diameters, and tapers may be fabricated according to the present invention. In exemplary embodiments, lengths of the instruments (from non-cutting tip to the end of the shaft portion) may be between about 19 mm and about 31 mm, and more preferably between about 21 mm and about 30 mm. In exemplary embodiments, the minimum diameter of the cutting surface may be between about 0.15 mm and about 0.70 mm, and more preferably between about 0.25 mm and about 0.65 mm. Further, in exemplary embodiments, the maximum diameter of the cutting surface may be between about 1.0 mm and about 2.0 mm, and more preferably between about 0.85 mm and about 1.60 mm. The taper ratio in exemplary embodiments may be between about 0.06 mm/mm and about 0.15 mm/mm, and more preferably between about 0.067 mm/mm and about 0.133 mm/mm.

To aid in easily identifying desired length, taper and cutting diameters, various markings and color schemes may be adopted and applied to the instruments. For example, the latch attachment of an instrument may be color coded to indicate the taper of the instrument, and the location of the color (e.g., coloration on the proximal third, middle third, or distal third of the attachment) may indicate the instrument number (i.e., first, second, or third instrument). Further, the shank of an instrument may have markings and/or a rubber stop, for example, to indicate length of the instrument and/or the depth of penetration during use.

It is to be understood that various combinations of the exemplary dimensions discussed above may be used to create files according to the present invention. The discussion below relates to illustrative embodiments of files according to the present invention.

FIG. 1 is a side view of a first, or most apical, instrument 10. As shown in FIG. 1, the first instrument 10 includes a non-cutting portion 20, a cutting surface 30, a shaft portion 40, a shank 50, and a latch attachment 60. The shank 50 may include a series of markings 53, indicating length to the non-cutting tip 20. The latch attachment 60 may include a forward color coded area, indicating that it is the first instrument of a set.

Figure 2:
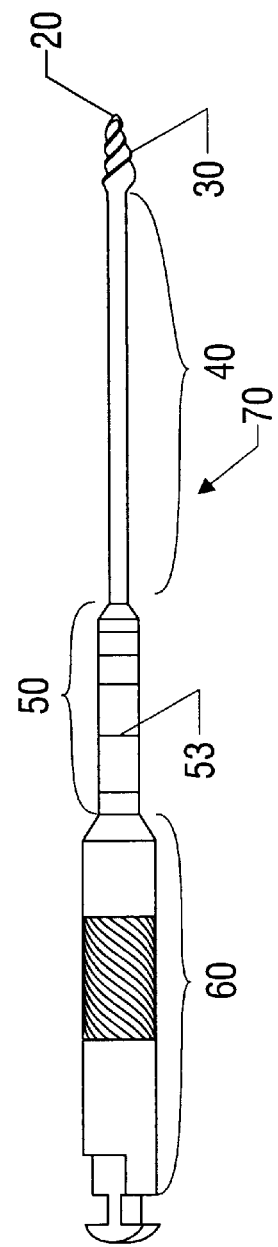
FIG. 2 is a side view of a middle instrument according to the present invention.
Figure 4:
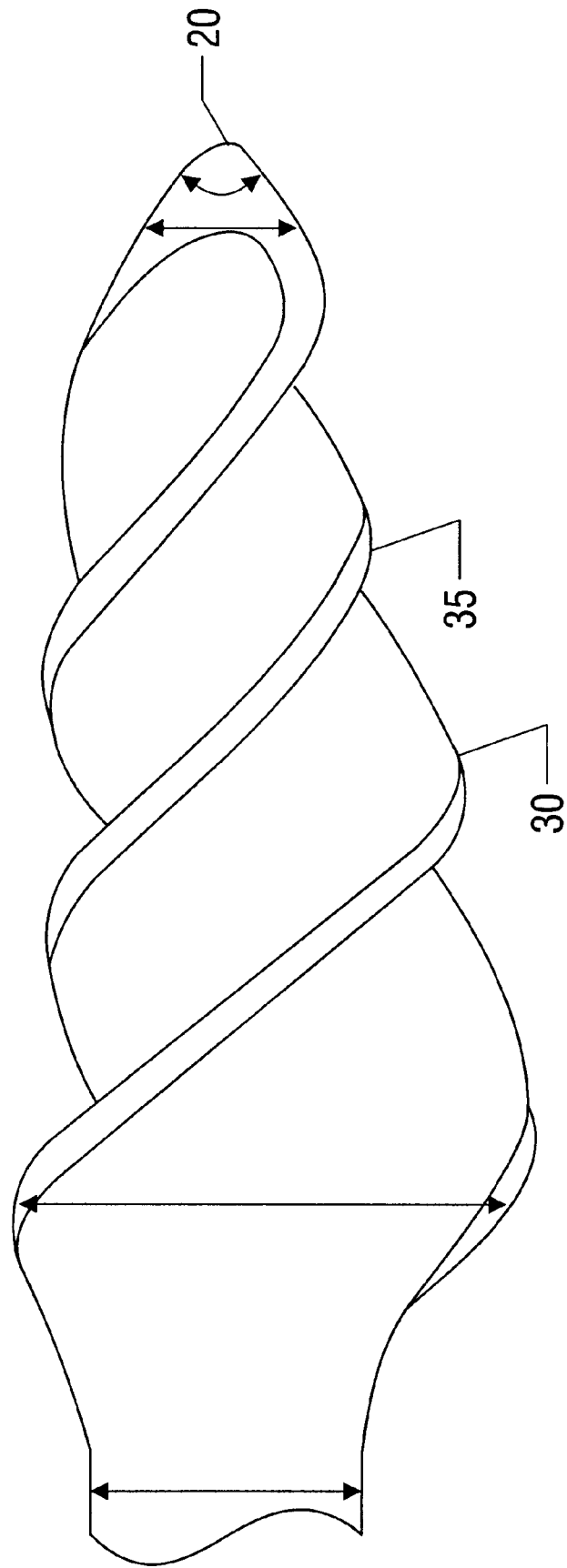
FIG. 4 is a close-up view of a cutting portion of an instrument according to the present invention.

In an exemplary embodiment, a 25 mm first instrument may have markings 53 on the shank 50 to signify various lengths, as shown in FIG. 1. A 21 mm first instrument may only have markings for 18, 19, and 20 mm, while the edge of the latch attachment 60 may signify 21 mm. A 30 mm first instrument may have the same markings as the 25 mm instrument, with the addition of rings for 25, 27, and 29 mm, and the edge of the latch attachment 60 may signify 30 mm. The latch attachment 60 may be a silver metal color with the distal one-third color coded. In exemplary embodiments, the color may signify the taper of the instrument as follows:

0.067 Taper may be Yellow
0.080 Taper may be Red
0.100 Taper may be Blue
0.133 Taper may be Green The minimum diameter of the cutting surface 30 of a first instrument 10 may be between about 0.15 mm and about 0.30 mm, and more preferably about 0.25 mm. The maximum diameter of the cutting surface 30 may be between about 0.30 mm and about 0.60 mm, and more preferably about 0.45 mm. The shaft 40 of a first instrument may be about 0.40 mm in diameter, and may be smooth and non-cutting, as shown in the close-up of FIG. 4. The length of the cutting surface 30 is proportional to the taper of the instrument. In exemplary embodiments, the cutting surface length may relate to taper as follows:

0.067 Taper may be 3 mm in length
0.080 Taper may be 2.5 mm in length
0.100 Taper may be 2.0 mm in length
0.133 Taper may be 1.5 mm in length FIG. 2 is a side view of a second, or middle instrument 70. A 25 mm second instrument will have markings 53 on the shank 50 to signify various lengths, as shown in FIG. 2. A 21 mm instrument may only have markings for 15, 16, 17, 18, 19, and 20 mm, while the edge of the latch attachment 60 may signify 21 mm. A 30 mm instrument may have the same markings as the 25 mm instrument, with the addition of rings for 25, 27, and 29 mm, and the edge of the latch attachment 60 may signify 30 mm. The latch attachment 60 may have the middle one-third color coded. In exemplary embodiments, the color scheme may be the same as described above.

The minimum diameter of the cutting surface 30 of a second instrument 70 may be between about 0.30 mm and about 0.60 mm, and more preferably about 0.45 mm. The maximum diameter of the cutting surface 30 may be about 0.50 mm and about 0.80 mm, and more preferably between about 0.65 mm. The shaft 40 of a second instrument may be about 0.60 mm in diameter and may be smooth and non-cutting, as shown in the close-up of FIG. 4. The length of the cutting surface 30 is dependent on the taper. In exemplary embodiments, the cutting surface length may be equal to the cutting surface length of a first instrument having the same taper.

Figure 3:
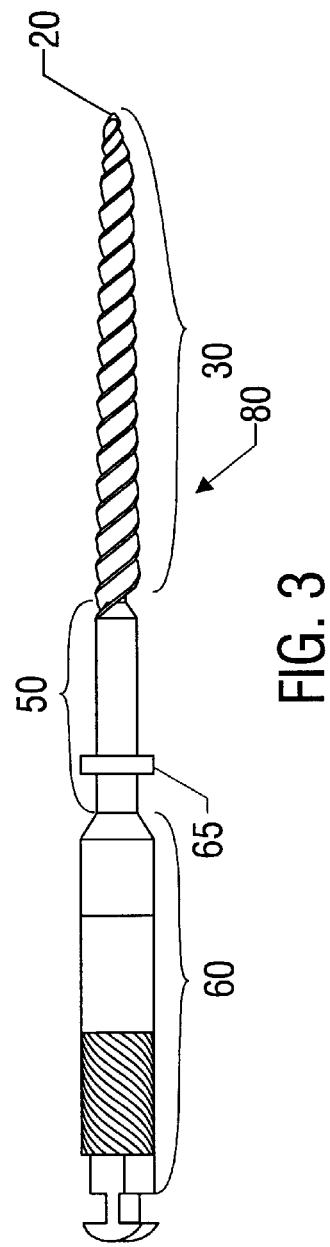
FIG. 3 is a side view of a most coronal instrument according to the present invention.

FIG. 3 is a side view of a third, or most coronal instrument 80, which may have a longer cutting surface 30 than that of the first two instruments. In an exemplary embodiment, it may not have a shaft 40 that is narrower than the largest diameter of the cutting surface 30, rather it may have a shank 50 that is substantially the same diameter as the largest diameter of the cutting surface 30. Instead of markings, the shank 50 of the third instrument 80 may have a rubber stop 65 to be set at a desired length to indicate the depth of penetration (i.e., stopping length). In exemplary embodiments, the length and diameters of the cutting surfaces may be as shown in TABLE 1.

TABLE 1

| TAPER (mm/mm) | MINIMUM DIAMETER OF THE CUTTING SURFACE | MAXIMUM DIAMETER OF THE CUTTING SURFACE | LENGTH OF THE CUTTING SURFACE |
| --- | --- | --- | --- |
| .067 | .65 mm | 1.32 mm | 10.0 mm |
| .080 | .65 mm | 1.33 mm | 8.5 mm |
| .100 | .65 mm | 1.50 mm | 8.5 mm |
| .133 | .65 mm | 1.51 mm | 6.5 mm |

The latch attachment 60 may have the proximal one-third portion color coded. In exemplary embodiments, the color may be the same colors discussed above. These instruments (i.e., the third instrument 80) may include lengths of between 21 mm and 25 mm.

In operation, the method of using instruments of the present invention will be in a crown down fashion (i.e., coronal to apical direction). The instruments may be used such that the smallest diameter instrument (i.e., the first instrument 10) will be taken to the cementodentinal junction ("CDJ") in the root canal. The next instrument (i.e., the middle instrument 70) will be taken to the corresponding point short of the CDJ (i.e., on a 0.067 taper instrument, approximately 3 mm from the CDJ, on a 0.080 taper, approximately 2.5 mm, etc.). Then the third instrument 80 will be taken to its corresponding point (i.e., on the 0.067 taper instrument that point would be 6 mm from the CDJ, on the 0.080 taper it would be 5 mm, etc.). This will thus lead to a continuous taper as chosen by the operator. Because the different tapers have the same tip sizes, the taper can be changed, for example, the apical extent of the root canal could have a 0.080 taper and then the rest could have a 0.067 taper. Thus, the different tapers are interchangeable.

TABLE 2 summarizes the sizes and tapers of illustrative instruments according to the present invention.

TABLE 2

| Taper (mm/mm) | Most Apical (First Instrument) | Middle (Second Instrument) | Most Coronal (Third Instrument) | Total Cutting Length of the Three Instruments |
| --- | --- | --- | --- | --- |
| .067 | Size 25–45 | Size 45–65 | Size 65–132 | 16.0 mm |
|  | Cutting tip is 3.0 mm long | Cutting tip is 3.0 mm long | Cutting tip is 10.0 mm long |  |
| .080 | Size 25–45 | Size 45–65 | Size 65–133 | 13.5 mm |
|  | Cutting tip is 2.5 mm long | Cutting tip is 2.5 mm long | Cutting tip is 8.5 mm long |  |
| .100 | Size 25–45 | Size 45–65 | Size 65–150 | 12.5 mm |
|  | Cutting tip is 2.0 mm long | Cutting tip is 2.0 mm long | Cutting tip is 8.5 mm long |  |
| .133 | Size 25–45 | Size 45–65 | Size 65–151 | 9.5 mm |
|  | Cutting tip is 1.5 mm long | Cutting tip is 1.5 mm long | Cutting tip is 6.5 mm long |  |

(Sizes are diameters in 1/100 mm)

TABLE 3, shown below, comprises a comparison of several instruments. Specifically, TABLE 3 compares use of two prior art files, namely instruments manufactured by Quantec and Profile, and a prototype instrument manufactured according to the present invention. As shown in TABLE 3, cross-sectional area and perimeter of a root canal is measured at several locations within the canal before and after preparation with the selected instrument. Roundness is also measured, with a value of 1 meaning a perfectly round cross-section. The centroid values relate to X and Y positions on a Cartesian coordinate system of the cross-section centroid before and after preparation, and movement of this centroid.

TABLE 3

|  | Object | Area | Perimeter | Major Axis | Minor Axis | Elongation | Roundness | Feret Diameter | Centroid | Movement of centroid |
| --- | --- | --- | --- | --- | --- | --- | --- | --- | --- | --- |
| Quantec #1 |  |  |  |  |  |  |  |  |  |  |
| Level 1 | Original | 0.06 | 0.95 | 0.31 | 0.25 | 1.25 | 0.85 | 0.28 | −155,347 | 25.3 |
| Buccal | Instr | 0.2 | 1.77 | 0.67 | 0.37 | 1.82 | 0.79 | 0.5 | −144,308 |  |
| Level 1 | Original | 0.02 | 0.57 | 0.21 | 0.13 | 1.55 | 0.9 | 0.17 | −435,292 | 9.85 |
| Lingual | Instr | 0.08 | 1.07 | 0.35 | 0.3 | 1.19 | 0.92 | 0.33 | −456,274 |  |
| Level 2 | Original | 0.07 | 1.03 | 0.4 | 0.24 | 1.66 | 0.86 | 0.3 | −147,305 | 9.85 |
| Buccal | Instr | 0.24 | 1.95 | 0.68 | 0.47 | 1.46 | 0.78 | 0.55 | −133,284 |  |
| Level 2 | Original | 0.04 | 0.78 | 0.29 | 0.16 | 1.76 | 0.83 | 0.23 | −497,246 | 11.4 |
| Lingual | Instr | 0.17 | 1.53 | 0.49 | 0.43 | 1.12 | 0.93 | 0.47 | −504,293 |  |
| Level 3 | Original | 0.3 | 2.3 | 0.9 | 0.4 | 2.25 | 0.71 | 0.62 | −146,324 | 15.3 |
| Buccal | Instr | 0.57 | 3.24 | 1.21 | 0.6 | 2.02 | 0.69 | 0.86 | −167,243 |  |
| Level 3 | Original | 0.23 | 1.95 | 0.72 | 0.4 | 1.8 | 0.77 | 0.54 | −503,318 | 2.33 |
| Lingual | Instr | 0.36 | 2.39 | 0.89 | 0.61 | 1.45 | 0.79 | 0.68 | −510,230 |  |
| Quantec #2 |  |  |  |  |  |  |  |  |  |  |
| Level 1 | Original | 0.03 | 0.69 | 0.25 | 0.15 | 1.62 | 0.81 | 0.2 | −222,310 | 5 |
| Lingual | Instr | 0.02 | 0.45 | 0.15 | 0.14 | 1.1 | 1.02 | 0.14 | −217,335 |  |

TABLE 3-continued

| | Object | Area | Perimeter | Major Axis | Minor Axis | Elongation | Roundness | Feret Diameter | Centroid | Movement of centroid |
|---|---|---|---|---|---|---|---|---|---|---|
| Level 1 | Original | 0.03 | 0.69 | 0.23 | 0.18 | 1.26 | 0.85 | 0.2 | −404,302 | 1.79 |
| Buccal | Instr | 0.09 | 1.14 | 0.4 | 0.3 | 1.32 | 0.88 | 0.34 | −398,324 | |
| Level 2 | Original | 0.2 | 1.73 | 0.65 | 0.39 | 1.67 | 0.82 | 0.5 | −184,288 | 12.17 |
| Lingual | Instr | 0.32 | 2.28 | 0.81 | 0.52 | 1.56 | 0.76 | 0.63 | −139,273 | |
| Level 2 | Original | 0.11 | 1.28 | 0.47 | 0.32 | 1.48 | 0.86 | 0.38 | −468,279 | 19.85 |
| Buccal | Instr | 0.31 | 2.57 | 0.92 | 0.48 | 1.9 | 0.58 | 0.63 | −448,267 | |
| Level 3 | Original | 0.19 | 1.65 | 0.57 | 0.46 | 1.26 | 0.88 | 0.49 | −507,261 | 18.03 |
| Buccal | Instr | 0.34 | 2.4 | 0.74 | 0.62 | 1.19 | 0.74 | 0.66 | −494,289 | |
| Level 3 | Original | 0.13 | 1.42 | 0.5 | 0.37 | 1.37 | 0.84 | 0.41 | −109,267 | 16.55 |
| Lingual | Instr | 0.32 | 2.17 | 0.7 | 0.61 | 1.13 | 0.85 | 0.64 | −99,289 | |
| Quantec #3 | | | | | | | | | | |
| Level 1 | Original | 0.04 | 0.89 | 0.29 | 0.22 | 1.32 | 0.66 | 0.23 | −225,236 | 10.63 |
| Buccal | Instr | 0.09 | 1.15 | 0.41 | 0.31 | 1.33 | 0.89 | 0.35 | −159,269 | |
| Level 1 | Original | 0.01 | 0.27 | 0.08 | 0.08 | 1.1 | 0.94 | 0.08 | −468,230 | 10.2 |
| Lingual | Instr | 0.11 | 1.23 | 0.39 | 0.37 | 1.06 | 0.95 | 0.38 | −419,266 | |
| Level 2 | Original | 0.08 | 1.06 | 0.37 | 0.27 | 1.37 | 0.86 | 0.31 | −154,276 | 7.21 |
| Buccal | Instr | 0.16 | 1.61 | 0.49 | 0.45 | 1.1 | 0.75 | 0.44 | −135,280 | |
| Level 2 | Original | 0.05 | 0.87 | 0.3 | 0.21 | 1.43 | 0.91 | 0.26 | −435,263 | 8.49 |
| Lingual | Instr | 0.15 | 1.46 | 0.47 | 0.42 | 1.13 | 0.9 | 0.44 | −417,269 | |
| Level 3 | Original | 0.11 | 1.61 | 0.65 | 0.27 | 2.42 | 0.54 | 0.37 | −118,318 | 44 |
| Buccal | Instr | 0.39 | 3.21 | 1.12 | 0.64 | 1.74 | 0.48 | 0.71 | −187,296 | |
| Level 3 | Original | 0.2 | 2.81 | 1.25 | 0.2 | 6.18 | 0.32 | 0.51 | −381,297 | 14 |
| Lingual | Instr | 0.43 | 3.2 | 1.23 | 0.62 | 1.97 | 0.52 | 0.74 | −408,307 | |
| Quantec #4 | | | | | | | | | | |
| Level 1 | Original | 0.09 | 1.14 | 0.39 | 0.31 | 1.26 | 0.89 | 0.34 | −353,281 | 15.65 |
| Buccal | Instr | 0.28 | 3.48 | 0.91 | 0.48 | 1.87 | 0.29 | 0.6 | −375,244 | |
| Level 1 | Original | 0 | 0.23 | 0.08 | 0.04 | 1.71 | 0.79 | 0.06 | −111,274 | 0 |
| Lingual | Instr | 0.14 | 1.9 | 0.64 | 0.33 | 1.93 | 0.49 | 0.42 | −146,199 | |
| Level 2 | Original | 0.01 | 0.41 | 0.14 | 0.11 | 1.22 | 1.06 | 0.13 | −176,262 | 7.21 |
| Lingual | Instr | 0.18 | 1.66 | 0.6 | 0.37 | 1.6 | 0.81 | 0.48 | −173,340 | |
| Level 2 | Original | 0.02 | 0.48 | 0.17 | 0.12 | 1.36 | 0.86 | 0.14 | −425,233 | 13 |
| Buccal | Instr | 0.22 | 1.76 | 0.58 | 0.49 | 1.19 | 0.9 | 0.53 | −422,300 | |
| Level 3 | Original | 0.02 | 0.52 | 0.16 | 0.14 | 1.18 | 0.88 | 0.16 | −174,262 | 11.18 |
| Lingual | Instr | 0.25 | 1.84 | 0.6 | 0.54 | 1.12 | 0.92 | 0.56 | −231,302 | |
| Level 3 | Original | 0.02 | 0.49 | 0.16 | 0.13 | 1.24 | 0.91 | 0.15 | −426,229 | 12.17 |
| Buccal | Instr | 0.29 | 2 | 0.63 | 0.6 | 1.04 | 0.9 | 0.61 | −418,294 | |
| Quantec #5 | | | | | | | | | | |
| Level 1 | Original | 0.02 | 0.55 | 0.19 | 0.14 | 1.31 | 0.93 | 0.17 | −428,334 | 20.12 |
| Buccal | Instr | 0.23 | 1.75 | 0.57 | 0.5 | 1.13 | 0.93 | 0.54 | −432,293 | |
| Level 1 | Original | 0.03 | 0.59 | 0.2 | 0.17 | 1.18 | 0.96 | 0.19 | −173,259 | 21.02 |
| Lingual | Instr | 0.06 | 0.91 | 0.3 | 0.27 | 1.12 | 0.86 | 0.27 | −196,268 | |
| Level 2 | Original | 0.14 | 1.43 | 0.51 | 0.35 | 1.48 | 0.86 | 0.42 | −445,284 | 20.52 |
| Buccal | Instr | 0.31 | 2.24 | 0.85 | 0.51 | 1.66 | 0.76 | 0.62 | −455,283 | |
| Level 2 | Original | 0.06 | 0.97 | 0.29 | 0.24 | 1.19 | 0.74 | 0.27 | −157,265 | 13.42 |
| Lingual | Instr | 0.22 | 1.79 | 0.6 | 0.45 | 1.34 | 0.87 | 0.53 | −148,307 | |
| Level 3 | Original | 0.26 | 1.97 | 0.72 | 0.43 | 1.69 | 0.83 | 0.57 | −160,252 | 11.4 |
| Lingual | Instr | 0.48 | 2.67 | 0.94 | 0.63 | 1.47 | 0.84 | 0.78 | −126,287 | |
| Level 3 | Original | 0.24 | 1.95 | 0.64 | 0.48 | 1.32 | 0.8 | 0.55 | −494,238 | 6.32 |
| Buccal | Instr | 0.4 | 2.39 | 0.8 | 0.66 | 1.21 | 0.89 | 0.72 | −467,285 | |
| Quantec #6 | | | | | | | | | | |
| Level 1 | Original | 0.02 | 0.53 | 0.18 | 0.12 | 1.48 | 0.77 | 0.15 | −536,315 | 7.07 |
| Buccal | Instr | 0.02 | 0.56 | 0.17 | 0.14 | 1.23 | 0.86 | 0.16 | −519,296 | |
| Level 1 | Original | 0.04 | 0.73 | 0.23 | 0.22 | 1.06 | 0.97 | 0.23 | −129,228 | 7.81 |
| Lingual | Instr | 0.05 | 0.85 | 0.27 | 0.25 | 1.09 | 0.93 | 0.26 | −113,198 | |
| Level 2 | Original | 0.04 | 0.75 | 0.27 | 0.17 | 1.53 | 0.88 | 0.22 | −86,334 | 8.06 |
| Lingual | Instr | 0.27 | 1.95 | 0.66 | 0.54 | 1.23 | 0.9 | 0.59 | −75,294 | |
| Level 2 | Original | 0.2 | 2.41 | 1.02 | 0.31 | 3.31 | 0.44 | 0.51 | −497,267 | 13 |
| Buccal | Instr | 0.23 | 1.99 | 0.64 | 0.5 | 1.28 | 0.74 | 0.55 | −499,292 | |
| Level 3 | Original | 0.22 | 7.5 | 2.64 | 0.87 | 3.04 | 0.05 | 0.53 | −311,233 | 7.81 |
| Middle | Instr | 0.09 | 2.12 | 0.98 | 0.1 | 9.95 | 0.24 | 0.33 | −307,292 | |
| Level 3 | Original | 0.12 | 1.51 | 0.62 | 0.23 | 2.69 | 0.65 | 0.39 | −133,262 | 7.07 |
| Lingual | Instr | 0.35 | 2.36 | 0.85 | 0.6 | 1.42 | 0.8 | 0.67 | −133,307 | |
| Level 3 | Original | 0.28 | 2.57 | 1.08 | 0.36 | 3.03 | 0.53 | 0.6 | −487,221 | 10.3 |
| Buccal | Instr | 0.35 | 2.55 | 0.95 | 0.61 | 1.56 | 0.68 | 0.67 | −474,304 | |
| Profile #1 | | | | | | | | | | |
| Level 1 | Original | 0.04 | 0.73 | 0.23 | 0.19 | 1.25 | 0.89 | 0.22 | −180,257 | 10 |
| Buccal | Instr | 0.11 | 1.22 | 0.42 | 0.33 | 1.27 | 0.92 | 0.37 | −162,296 | |
| Level 1 | Original | 0.04 | 0.71 | 0.24 | 0.18 | 1.37 | 0.89 | 0.21 | −328,246 | 12.21 |
| Lingual | Instr | 0.07 | 0.95 | 0.3 | 0.29 | 1.03 | 0.93 | 0.29 | −329,293 | |
| Level 2 | Original | 0.12 | 1.46 | 0.59 | 0.25 | 2.36 | 0.72 | 0.39 | −206,285 | 18.36 |
| Buccal | Instr | 0.32 | 2.13 | 0.66 | 0.62 | 1.08 | 0.89 | 0.64 | −172,233 | |
| Level 2 | Original | 0.17 | 1.67 | 0.64 | 0.36 | 1.78 | 0.76 | 0.46 | −426,265 | 10.82 |

TABLE 3-continued

|  | Object | Area | Perimeter | Major Axis | Minor Axis | Elongation | Roundness | Feret Diameter | Centroid | Movement of centroid |
|---|---|---|---|---|---|---|---|---|---|---|
| Lingual | Instr | 0.2 | 1.7 | 0.54 | 0.47 | 1.14 | 0.86 | 0.5 | −394,258 | |
| Level 3 | Original | 0.12 | 1.61 | 0.67 | 0.25 | 2.69 | 0.56 | 0.38 | −425,297 | 14.56 |
| Lingual | Instr | 0.61 | 2.93 | 0.92 | 0.88 | 1.05 | 0.89 | 0.88 | −427,245 | |
| Level 3 | Original | 0.13 | 1.78 | 0.75 | 0.24 | 3.09 | 0.53 | 0.41 | −166,270 | 4.47 |
| Buccal | Instr | 0.62 | 2.96 | 0.92 | 0.88 | 1.05 | 0.89 | 0.89 | −156,239 | |
| Profile #2 | | | | | | | | | | |
| Level 1 | Original | 0.05 | 0.92 | 0.35 | 0.19 | 1.88 | 0.78 | 0.26 | −179,314 | 7.62 |
| Buccal | Instr | 0.16 | 1.6 | 0.52 | 0.45 | 1.15 | 0.8 | 0.45 | −204,263 | |
| Level 1 | Original | 0.06 | 0.95 | 0.36 | 0.18 | 1.99 | 0.83 | 0.28 | −324,308 | 10.82 |
| Lingual | Instr | 0.13 | 1.35 | 0.44 | 0.39 | 1.13 | 0.93 | 0.41 | −364,270 | |
| Level 2 | Original | 0.81 | 9.38 | 2.74 | 0.99 | 2.76 | 0.12 | 1.02 | −282,259 | 8.06 |
| Single | Instr | 1.24 | 7.56 | 3.05 | 0.68 | 4.49 | 0.27 | 1.26 | −309,293 | |
| Level 3 | Original | 0.15 | 1.74 | 0.71 | 0.27 | 2.6 | 0.61 | 0.43 | −433,288 | 17.69 |
| Lingual | Instr | 1.16 | 4.09 | 1.26 | 1.17 | 1.07 | 0.87 | 1.22 | −438,291 | |
| Level 3 | Original | 0.2 | 1.98 | 0.8 | 0.29 | 2.73 | 0.63 | 0.5 | −165,247 | 13.42 |
| Buccal | Instr | 0.85 | 3.47 | 1.09 | 1.01 | 1.08 | 0.89 | 1.04 | −161,290 | |
| Profile #3 | | | | | | | | | | |
| Level 1 | Original | 0.06 | 1.14 | 0.42 | 0.19 | 2.25 | 0.62 | 0.29 | −360,308 | 7.81 |
| Buccal | Instr | 0.07 | 0.96 | 0.31 | 0.28 | 1.1 | 0.91 | 0.29 | −440,294 | |
| Level 1 | Original | 0.02 | 0.61 | 0.19 | 0.11 | 1.73 | 0.54 | 0.14 | −212,262 | 2.68 |
| Lingual | Instr | 0.04 | 0.86 | 0.26 | 0.22 | 1.16 | 0.75 | 0.24 | −280,266 | |
| Level 2 | Original | 0.06 | 0.91 | 0.31 | 0.23 | 1.35 | 0.86 | 0.27 | −204,276 | 10 |
| Lingual | Instr | 0.22 | 1.74 | 0.55 | 0.5 | 1.09 | 0.9 | 0.52 | −171,249 | |
| Level 2 | Original | 0.03 | 0.63 | 0.21 | 0.18 | 1.13 | 1.02 | 0.2 | −473,256 | 14.32 |
| Buccal | Instr | 0.19 | 1.63 | 0.53 | 0.47 | 1.13 | 0.92 | 0.5 | −460,269 | |
| Level 3 | Original | 0.06 | 0.93 | 0.31 | 0.24 | 1.29 | 0.88 | 0.28 | −503,319 | 2.47 |
| Buccal | Instr | 0.37 | 2.24 | 0.73 | 0.63 | 1.17 | 0.92 | 0.68 | −486,293 | |
| Level 3 | Original | 0.09 | 1.11 | 0.35 | 0.31 | 1.13 | 0.89 | 0.33 | −102,269 | 6.71 |
| Lingual | Instr | 0.41 | 2.39 | 0.75 | 0.73 | 1.03 | 0.9 | 0.72 | −91,278 | |
| Profile #4 | | | | | | | | | | |
| Level 1 | Original | 0.03 | 0.69 | 0.22 | 0.16 | 1.35 | 0.69 | 0.18 | −218,301 | 1.67 |
| Lingual | Instr | 0.07 | 0.99 | 0.31 | 0.29 | 1.05 | 0.88 | 0.3 | −229,263 | |
| Level 1 | Original | 0.05 | 0.82 | 0.28 | 0.23 | 1.23 | 0.89 | 0.25 | −381,227 | 6.4 |
| Buccal | Instr | 0.08 | 0.67 | 0.22 | 0.2 | 1.12 | 0.97 | 0.21 | −390,182 | |
| Level 2 | Original | 0.57 | 7.72 | 2.33 | 0.83 | 2.8 | 0.12 | 0.85 | −306,248 | 28.64 |
| Single | Instr | 0.75 | 6.13 | 2.26 | 0.73 | 3.11 | 0.25 | 0.97 | −255,270 | |
| Level 3 | Original | 0.2 | 2.74 | 1.18 | 0.21 | 5.68 | 0.34 | 0.51 | −238,264 | 13 |
| Lingual | Instr | 0.72 | 3.41 | 1.07 | 0.91 | 1.17 | 0.78 | 0.96 | −188,334 | |
| Level 3 | Original | 0.27 | 3.17 | 1.39 | 0.26 | 5.33 | 0.34 | 0.59 | −381,268 | 18.36 |
| Buccal | Instr | 0.86 | 3.48 | 1.12 | 0.98 | 1.14 | 0.9 | 1.05 | −310,315 | |
| Profile #5 | | | | | | | | | | |
| Level 1 | Original | 0.02 | 0.5 | 0.17 | 0.15 | 1.17 | 0.99 | 0.16 | −290,299 | 10.82 |
| Lingual | Instr | 0.05 | 0.79 | 0.28 | 0.2 | 1.42 | 0.91 | 0.24 | −254,221 | |
| Level 1 | Original | 0.01 | 0.31 | 0.11 | 0.07 | 1.65 | 0.92 | 0.09 | −211,296 | 8.06 |
| Buccal | Instr | 0.06 | 0.93 | 0.29 | 0.27 | 1.09 | 0.89 | 0.28 | −191,220 | |
| Level 2 | Original | 0.04 | 0.72 | 0.24 | 0.21 | 1.14 | 0.85 | 0.21 | −414,277 | 19.21 |
| Lingual | Instr | 0.33 | 2.16 | 0.72 | 0.61 | 1.19 | 0.9 | 0.65 | −361,289 | |
| Level 2 | Original | 0.07 | 1.01 | 0.35 | 0.24 | 1.44 | 0.84 | 0.29 | −213,243 | 14.32 |
| Buccal | Instr | 0.27 | 2.02 | 0.67 | 0.53 | 1.26 | 0.85 | 0.59 | −144,271 | |
| Level 3 | Original | 0.16 | 1.49 | 0.49 | 0.42 | 1.16 | 0.88 | 0.45 | −143,261 | 6.71 |
| Buccal | Instr | 0.46 | 2.53 | 0.81 | 0.73 | 1.11 | 0.89 | 0.76 | −155,272 | |
| Level 3 | Original | 0.23 | 1.81 | 0.6 | 0.51 | 1.18 | 0.88 | 0.54 | −441,249 | 8.92 |
| Lingual | Instr | 0.47 | 2.55 | 0.8 | 0.75 | 1.06 | 0.91 | 0.77 | −443,266 | |
| Profile #6 | | | | | | | | | | |
| Lingual | Original | 0.02 | 0.43 | 0.15 | 0.13 | 1.1 | 1.05 | 0.14 | −481,298 | 3.24 |
| Level 1 | Instr | 0.02 | 0.51 | 0.16 | 0.14 | 1.17 | 0.91 | 0.16 | −494,258 | |
| Buccal | Original | 0.06 | 0.93 | 0.31 | 0.23 | 1.32 | 0.88 | 0.28 | −179,287 | 0 |
| Level 1 | Instr | 0.06 | 0.95 | 0.31 | 0.23 | 1.35 | 0.73 | 0.26 | −186,269 | |
| Lingual | Original | 0.08 | 1.24 | 0.44 | 0.24 | 1.81 | 0.65 | 0.32 | −472,304 | 1.35 |
| Level 2 | Instr | 0.23 | 1.8 | 0.57 | 0.54 | 1.06 | 0.9 | 0.54 | −468,268 | |
| Buccal | Original | 0.03 | 0.65 | 0.22 | 0.14 | 1.6 | 0.75 | 0.18 | −166,292 | 5 |
| Level 2 | Instr | 0.21 | 1.76 | 0.55 | 0.49 | 1.13 | 0.86 | 0.52 | −159,262 | |
| Lingual | Original | 0.09 | 1.24 | 0.47 | 0.25 | 1.9 | 0.76 | 0.34 | −430,283 | 16.12 |
| Level 3 | Instr | 0.62 | 3.21 | 0.94 | 0.88 | 1.07 | 0.75 | 0.89 | −454,317 | |
| Buccal | Original | 0.17 | 1.76 | 0.72 | 0.31 | 2.36 | 0.69 | 0.46 | −191,259 | 9.49 |
| Level 3 | Instr | 0.59 | 3.01 | 0.92 | 0.85 | 1.08 | 0.81 | 0.86 | −208,294 | |
| Prototype (.080) #1 | | | | | | | | | | |
| Level 1 | Original | 0.1 | 1.69 | 0.72 | 0.18 | 3.99 | 0.44 | 0.36 | −242,231 | 3.16 |
| Single | Instr | 0.12 | 1.49 | 0.59 | 0.26 | 2.23 | 0.68 | 0.39 | −283,239 | |
| Level 2 | Original | 0.1 | 1.24 | 0.39 | 0.35 | 1.1 | 0.83 | 0.36 | −187,322 | 15 |
| Buccal | Instr | 0.54 | 2.83 | 0.93 | 0.77 | 1.2 | 0.85 | 0.83 | −222,211 | |

TABLE 3-continued

| | Object | Area | Perimeter | Major Axis | Minor Axis | Elongation | Roundness | Feret Diameter | Centroid | Movement of centroid |
|---|---|---|---|---|---|---|---|---|---|---|
| Level 2 | Original | 0.03 | 0.63 | 0.2 | 0.19 | 1.05 | 0.92 | 0.19 | −353,305 | 17.09 |
| Lingual | Instr | 0.52 | 2.72 | 0.9 | 0.78 | 1.16 | 0.89 | 0.82 | −404,203 | |
| Level 3 | Original | 0.08 | 1.09 | 0.35 | 0.28 | 1.23 | 0.85 | 0.32 | −414,302 | 5.83 |
| Lingual | Instr | 1.21 | 4.17 | 1.28 | 1.21 | 1.05 | 0.87 | 1.24 | −397,302 | |
| Level 3 | Original | 0.05 | 0.79 | 0.26 | 0.21 | 1.21 | 0.92 | 0.24 | −167,276 | 8 |
| Buccal | Instr | 1.1 | 4.05 | 1.25 | 1.08 | 1.15 | 0.84 | 1.18 | −146,317 | |
| Prototype (.080) #2 | | | | | | | | | | |
| Level 1 | Original | 0.06 | 0.91 | 0.31 | 0.24 | 1.26 | 0.93 | 0.28 | −273,316 | 0 |
| Buccal | Instr | 0.07 | 1.01 | 0.32 | 0.28 | 1.13 | 0.86 | 0.3 | −193,344 | |
| Level 1 | Original | 0.05 | 0.86 | 0.3 | 0.22 | 1.34 | 0.85 | 0.25 | −355,274 | |
| Lingual | | | | | | Unable to Instrument | | | | |
| Level 2 | Original | 0.21 | 1.73 | 0.59 | 0.47 | 1.27 | 0.87 | 0.51 | −210,286 | 10.2 |
| Buccal | Instr | 0.42 | 2.44 | 0.76 | 0.71 | 1.07 | 0.88 | 0.73 | −192,272 | |
| Level 2 | Original | 0.22 | 1.82 | 0.55 | 0.53 | 1.04 | 0.82 | 0.52 | −433,259 | |
| Lingual | | | | | | Unable to Instrument | | | | |
| Level 3 | Original | 0.2 | 1.8 | 0.66 | 0.41 | 1.61 | 0.77 | 0.5 | −119,277 | 5.39 |
| Buccal | Instr | 1.09 | 3.99 | 1.25 | 1.11 | 1.13 | 0.86 | 1.18 | −156,304 | |
| Level 3 | Original | 0.21 | 1.73 | 0.6 | 0.45 | 1.33 | 0.9 | 0.52 | −469,247 | 9.22 |
| Lingual | Instr | 0.45 | 2.56 | 0.79 | 0.71 | 1.12 | 0.86 | 0.76 | −480,301 | |
| Prototype (.080) #3 | | | | | | | | | | |
| Level 1 | Original | 0.14 | 2.75 | 1.04 | 0.27 | 3.8 | 0.23 | 0.42 | −340,248 | 5 |
| Buccal | Instr | 0.15 | 2.07 | 0.79 | 0.36 | 2.2 | 0.43 | 0.43 | −349,270 | |
| Level 1 | Original | 0.02 | 0.57 | 0.18 | 0.15 | 1.22 | 0.81 | 0.16 | −149,225 | 4.12 |
| Lingual | Instr | 0.09 | 1.13 | 0.36 | 0.34 | 1.08 | 0.94 | 0.35 | −167,232 | |
| Level 2 | Original | 0.08 | 1.39 | 0.49 | 0.27 | 1.84 | 0.49 | 0.31 | −386,206 | 15.65 |
| Buccal | Instr | 0.21 | 1.71 | 0.56 | 0.47 | 1.18 | 0.91 | 0.52 | −365,290 | |
| Level 2 | Original | 0.05 | 0.83 | 0.29 | 0.2 | 1.44 | 0.88 | 0.25 | −201,197 | 9.22 |
| Lingual | Instr | 0.17 | 1.59 | 0.49 | 0.46 | 1.05 | 0.85 | 0.47 | −159,298 | |
| Level 3 | Original | 0.12 | 1.34 | 0.45 | 0.34 | 1.32 | 0.83 | 0.39 | −423,322 | 4.47 |
| Buccal | Instr | 0.46 | 2.57 | 0.8 | 0.75 | 1.07 | 0.88 | 0.77 | −413,277 | |
| Level 3 | Original | 0.11 | 1.36 | 0.48 | 0.3 | 1.59 | 0.78 | 0.38 | −136,313 | 16.03 |
| Lingual | Instr | 0.52 | 2.77 | 0.86 | 0.78 | 1.11 | 0.85 | 0.81 | −146,287 | |
| Prototype (.080) #4 | | | | | | | | | | |
| Level 1 | Original | 0.05 | 0.88 | 0.32 | 0.18 | 1.74 | 0.74 | 0.24 | −392,276 | 6.4 |
| Lingual | Instr | 0.07 | 0.95 | 0.33 | 0.25 | 1.29 | 0.92 | 0.29 | −459,297 | |
| Level 1 | Original | 0.08 | 1.28 | 0.44 | 0.23 | 1.9 | 0.61 | 0.32 | −167,265 | 18.03 |
| Buccal | Instr | 0.14 | 1.41 | 0.44 | 0.4 | 1.1 | 0.9 | 0.43 | −216,319 | |
| Level 2 | Original | 0.12 | 1.35 | 0.43 | 0.39 | 1.1 | 0.86 | 0.4 | −141,296 | 16.16 |
| Buccal | Instr | 0.26 | 1.89 | 0.6 | 0.54 | 1.12 | 0.9 | 0.57 | −151,270 | |
| Level 2 | Original | 0.08 | 1.22 | 0.46 | 0.22 | 2.1 | 0.7 | 0.32 | −446,296 | 11.05 |
| Lingual | Instr | 0.18 | 1.56 | 0.51 | 0.43 | 1.19 | 0.9 | 0.47 | −488,277 | |
| Level 3 | Original | 0.3 | 2.27 | 0.8 | 0.48 | 1.67 | 0.73 | 0.62 | −158,301 | 7.81 |
| Buccal | Instr | 1.06 | 3.91 | 1.2 | 1.12 | 1.07 | 0.87 | 1.16 | −149,305 | |
| Level 3 | Original | 0.19 | 1.78 | 0.66 | 0.37 | 1.77 | 0.76 | 0.49 | −480,278 | 10 |
| Lingual | Instr | 0.66 | 3.07 | 0.96 | 0.91 | 1.06 | 0.88 | 0.92 | −467,316 | |
| Prototype (.080) #5 | | | | | | | | | | |
| Level 1 | Original | 0.14 | 2.01 | 0.82 | 0.28 | 2.96 | 0.44 | 0.42 | −243,313 | 19.92 |
| Single | Instr | 0.39 | 2.98 | 1.13 | 0.48 | 2.35 | 0.56 | 0.71 | −368,310 | |
| Level 2 | Original | 0.18 | 1.57 | 0.5 | 0.48 | 1.05 | 0.91 | 0.48 | −453,297 | 27.31 |
| Lingal | Instr | 0.59 | 3.08 | 1.16 | 0.68 | 1.71 | 0.79 | 0.87 | −456,257 | |
| Level 2 | Original | 0.26 | 2.04 | 0.73 | 0.46 | 1.59 | 0.78 | 0.57 | −186,282 | 11.66 |
| Buccal | Instr | 0.57 | 3.01 | 0.97 | 0.8 | 1.2 | 0.79 | 0.85 | −169,291 | |
| Level 3 | Original | 0.25 | 2.17 | 0.87 | 0.38 | 2.3 | 0.67 | 0.56 | −469,330 | 11.7 |
| Lingual | Instr | 1.11 | 3.98 | 1.27 | 1.13 | 1.12 | 0.88 | 1.19 | −447,322 | |
| Level 3 | Original | 0.18 | 3.64 | 1.61 | 0.24 | 6.78 | 0.17 | 0.47 | −162,305 | 20.62 |
| Buccal | Instr | 0.86 | 3.79 | 1.16 | 1.01 | 1.15 | 0.76 | 1.05 | −127,273 | |
| Prototype (.080) #6 | | | | | | | | | | |
| Level 1 | Original | 0.03 | 0.63 | 0.2 | 0.19 | 1.05 | 0.93 | 0.19 | −439,281 | 6.71 |
| Buccal | Instr | 0.11 | 1.26 | 0.4 | 0.36 | 1.12 | 0.93 | 0.38 | −406,237 | |
| Level 1 | Original | 0.03 | 0.71 | 0.26 | 0.14 | 1.93 | 0.75 | 0.2 | −154,263 | 0 |
| Lingual | Instr | 0.08 | 1.12 | 0.35 | 0.32 | 1.09 | 0.83 | 0.32 | −115,257 | |
| Level 2 | Original | 0.07 | 1.08 | 0.35 | 0.22 | 1.57 | 0.71 | 0.29 | −498,238 | 6.71 |
| Buccal | Instr | 0.23 | 1.81 | 0.57 | 0.53 | 1.09 | 0.88 | 0.54 | −483,274 | |
| Level 2 | Original | 0.08 | 1.09 | 0.36 | 0.27 | 1.32 | 0.81 | 0.31 | −143,223 | 10.2 |
| Lingual | Instr | 0.28 | 1.94 | 0.62 | 0.58 | 1.07 | 0.91 | 0.59 | −124,318 | |
| Level 3 | Original | 0.2 | 2.84 | 1.21 | 0.25 | 4.79 | 0.31 | 0.5 | −175,261 | 11.05 |
| Lingual | Instr | 0.66 | 3.14 | 0.98 | 0.91 | 1.08 | 0.85 | 0.92 | −206,313 | |
| Level 3 | Original | 0.17 | 1.61 | 0.56 | 0.4 | 1.39 | 0.82 | 0.46 | −443,249 | |
| Buccal | Instr | 0.48 | 2.63 | 0.81 | 0.77 | 1.06 | 0.88 | 0.78 | −493,279 | |
| Prototype (.067) #1 | | | | | | | | | | |
| Level 1 | Original | 0.19 | 1.7 | 0.54 | 0.51 | 1.05 | 0.8 | 0.49 | −276,298 | 0 |

TABLE 3-continued

|  | Object | Area | Perimeter | Major Axis | Minor Axis | Elongation | Roundness | Feret Diameter | Centroid | Movement of centroid |
|---|---|---|---|---|---|---|---|---|---|---|
| Single | Instr | 0.22 | 1.79 | 0.55 | 0.5 | 1.11 | 0.85 | 0.52 | −294,223 |  |
| Level 2 | Original | 0.13 | 1.36 | 0.44 | 0.39 | 1.13 | 0.89 | 0.41 | −176,269 | 22.02 |
| Lingual | Instr | 0.34 | 2.23 | 0.75 | 0.58 | 1.3 | 0.87 | 0.66 | −174,301 |  |
| Level 2 | Original | 0.28 | 2.12 | 0.77 | 0.52 | 1.47 | 0.79 | 0.6 | −372,232 | 7.62 |
| Buccal | Instr | 0.31 | 2.1 | 0.72 | 0.55 | 1.3 | 0.87 | 0.62 | −395,274 |  |
| Level 3 | Original | 0.24 | 1.93 | 0.73 | 0.41 | 1.76 | 0.81 | 0.55 | −143,299 | 23.09 |
| Lingual | Instr | 0.8 | 3.36 | 1.07 | 0.95 | 1.12 | 0.89 | 1.01 | −179,308 |  |
| Level 3 | Original | 0.18 | 1.6 | 0.55 | 0.45 | 1.23 | 0.86 | 0.47 | −444,284 | 6.4 |
| Buccal | Instr | 0.58 | 2.84 | 0.88 | 0.85 | 1.03 | 0.91 | 0.86 | −446,282 |  |
| Prototype (.067) #2 |  |  |  |  |  |  |  |  |  |  |
| Level 1 | Original | 0.05 | 0.89 | 0.34 | 0.19 | 1.79 | 0.85 | 0.26 | −440,135 | 12.04 |
| Lingual | Instr | 0.11 | 1.34 | 0.49 | 0.27 | 1.82 | 0.78 | 0.38 | −338,251 |  |
| Level 1 | Original | 0.03 | 0.77 | 0.29 | 0.14 | 2.03 | 0.71 | 0.21 | −292,142 | 31.02 |
| Buccal | Instr | 0.08 | 1.07 | 0.35 | 0.27 | 1.3 | 0.83 | 0.31 | −187,258 |  |
| Level 2 | Original | 0.16 | 1.99 | 0.84 | 0.26 | 3.17 | 0.51 | 0.45 | −381,279 | 14.32 |
| Lingual | Instr | 0.44 | 2.53 | 0.77 | 0.76 | 1.01 | 0.87 | 0.75 | −393,272 |  |
| Level 2 | Original | 0.13 | 2.09 | 0.89 | 0.21 | 4.27 | 0.38 | 0.41 | −233,265 | 7.07 |
| Buccal | Instr | 0.38 | 2.37 | 0.79 | 0.64 | 1.23 | 0.85 | 0.69 | −231,275 |  |
| Level 3 | Original | 0.58 | 6.83 | 2.49 | 0.66 | 3.79 | 0.16 | 0.86 | −290,314 | 0 |
| Single | Instr | 1.79 | 7.47 | 2.65 | 1 | 2.65 | 0.4 | 1.51 | −302,320 |  |
| Prototype (.067) #3 |  |  |  |  |  |  |  |  |  |  |
| Level 1 | Original | 0.04 | 0.85 | 0.34 | 0.14 | 2.37 | 0.72 | 0.23 | −476,278 | 0 |
| Lingual | Instr | 0.06 | 0.88 | 0.3 | 0.21 | 1.4 | 0.9 | 0.27 | −482,286 |  |
| Level 1 | Original | 0.03 | 0.64 | 0.2 | 0.16 | 1.31 | 0.78 | 0.18 | −167,252 | 5 |
| Buccal | Instr | 0.06 | 0.92 | 0.31 | 0.24 | 1.27 | 0.91 | 0.28 | −160,291 |  |
| Level 2 | Original | 0.05 | 1.07 | 0.35 | 0.24 | 1.44 | 0.53 | 0.25 | −494,250 | 9.22 |
| Lingual | Instr | 0.1 | 1.18 | 0.37 | 0.32 | 1.17 | 0.88 | 0.35 | −472,265 |  |
| Level 2 | Original | 0.09 | 1.17 | 0.44 | 0.27 | 1.62 | 0.82 | 0.34 | −118,251 | 14.32 |
| Buccal | Instr | 0.14 | 1.44 | 0.47 | 0.4 | 1.18 | 0.88 | 0.43 | −90,232 |  |
| Level 3 | Original | 0.11 | 1.2 | 0.39 | 0.36 | 1.07 | 0.95 | 0.37 | −468,276 | 17.03 |
| Lingual | Instr | 0.76 | 3.33 | 1.03 | 0.97 | 1.06 | 0.86 | 0.99 | −469,274 |  |
| Level 3 | Original | 0.16 | 1.5 | 0.5 | 0.4 | 1.26 | 0.9 | 0.45 | −99,271 | 5.1 |
| Buccal | Instr | 0.6 | 2.91 | 0.91 | 0.85 | 1.07 | 0.89 | 0.88 | −112,264 |  |
| Prototype (.067) #4 |  |  |  |  |  |  |  |  |  |  |
| Level 1 | Original | 0.06 | 0.91 | 0.3 | 0.25 | 1.19 | 0.92 | 0.28 | −191,271 | 9.06 |
| Buccal | Instr | 0.11 | 1.21 | 0.39 | 0.35 | 1.13 | 0.92 | 0.37 | −146,276 |  |
| Level 1 | Original | 0.07 | 0.98 | 0.33 | 0.27 | 1.23 | 0.92 | 0.3 | −483,237 | 5.1 |
| Lingual | Instr | 0.1 | 1.2 | 0.4 | 0.33 | 1.2 | 0.87 | 0.36 | −453,234 |  |
| Level 2 | Original | 0.19 | 1.65 | 0.52 | 0.48 | 1.09 | 0.87 | 0.49 | −468,303 | 5.1 |
| Lingual | Instr | 0.33 | 2.19 | 0.7 | 0.6 | 1.16 | 0.87 | 0.65 | −451,306 |  |
| Level 2 | Original | 0.2 | 1.68 | 0.56 | 0.48 | 1.17 | 0.91 | 0.51 | −115,275 | 7.07 |
| Buccal | Instr | 0.31 | 2.11 | 0.66 | 0.6 | 1.11 | 0.87 | 0.63 | −97,305 |  |
| Level 3 | Original | 0.34 | 2.63 | 1.1 | 0.38 | 2.91 | 0.61 | 0.66 | −194,296 | 16.49 |
| Buccal | Instr | 0.81 | 3.39 | 1.05 | 1.01 | 1.04 | 0.89 | 1.02 | −200,341 |  |
| Level | Original | 0.24 | 2.27 | 0.91 | 0.31 | 2.96 | 0.59 | 0.55 | −411,292 | 11.18 |
| Lingual | Instr | 0.76 | 3.27 | 1.06 | 0.89 | 1.19 | 0.89 | 0.98 | −440,327 |  |
| Prototype (.067) #5 |  |  |  |  |  |  |  |  |  |  |
| Level 1 | Original | 0.41 | 4.05 | 1.55 | 0.41 | 3.82 | 0.31 | 0.72 | −290,261 | 6.71 |
| Single | Instr | 0.48 | 3.87 | 1.53 | 0.42 | 3.64 | 0.41 | 0.78 | −279,305 |  |
| Level 2 | Original | 0.36 | 5.3 | 1.64 | 0.8 | 2.04 | 0.16 | 0.67 | −283,284 | 7.28 |
| Single | Instr | 0.42 | 3.93 | 1.61 | 0.41 | 3.97 | 0.34 | 0.73 | −276,249 |  |
| Level 3 | Original | 0.13 | 2.05 | 0.85 | 0.27 | 3.16 | 0.39 | 0.41 | −366,285 | 19.03 |
| Buccal | Instr | 0.52 | 2.72 | 0.93 | 0.73 | 1.28 | 0.88 | 0.81 | −336,273 |  |
| Level 3 | Original | 0.13 | 1.96 | 0.84 | 0.21 | 4.04 | 0.41 | 0.4 | −193,283 | 26.48 |
| Lingual | Instr | 0.51 | 3.09 | 1.06 | 0.74 | 1.42 | 0.67 | 0.81 | −207,285 |  |
| Prototype (.067) #6 |  |  |  |  |  |  |  |  |  |  |
| Level 1 | Original | 0.12 | 1.44 | 0.56 | 0.28 | 2.01 | 0.76 | 0.4 | −349,295 | 5.16 |
| Single | Instr | 0.16 | 1.48 | 0.48 | 0.41 | 1.17 | 0.92 | 0.45 | −333,329 |  |
| Level 2 | Original | 0.26 | 3.36 | 1.09 | 0.52 | 2.1 | 0.29 | 0.58 | −300,236 | 10.05 |
| Single | Instr | 0.43 | 2.5 | 0.78 | 0.7 | 1.12 | 0.86 | 0.74 | −343,250 |  |
| Level 3 | Original | 0.23 | 2.04 | 0.82 | 0.37 | 2.23 | 0.71 | 0.55 | −420,250 | 8.54 |
| Lingual | Instr | 0.95 | 3.69 | 1.16 | 1.04 | 1.12 | 0.88 | 1.1 | −394,243 |  |
| Level 3 |  | 0.15 | 1.44 | 0.47 | 0.43 | 1.1 | 0.89 | 0.43 | −161,224 |  |
| Buccal |  |  |  |  |  | Unable to Instrument |  |  |  |  |

Further modification and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having benefit of this description of the invention.

What is claimed is:

1. A successive set of endodontic instruments for preparing a root canal, comprising:
   a set of cutting surfaces, wherein
      a succeeding cutting surface has a minimum diameter distal portion substantially equal to a maximum diameter proximal portion of a preceding cutting surface,
      at least one of said cutting surfaces has a neutral rake angle, and
      at least one of said cutting surfaces has a non-cutting tip located adjacent said minimum diameter distal portion.

2. The successive set of endodontic instruments of claim 1, further comprising a shaft segment located adjacent said maximum diameter proximal portion.

3. The successive set of endodontic instruments of claim 2, further comprising a shank located adjacent said shaft segment.

4. The successive set of endodontic instruments of claim 3, further comprising markings on said shank indicating varying lengths of said instrument.

5. The successive set of endodontic instruments of claim 3, further comprising a stop located on said shank moveable to correspond to varying lengths of said instrument.

6. The successive set of endodontic instruments of claim 1, wherein said non-cutting tip prevents transportation of said root canal.

7. The successive set of endodontic instruments of claim 6, wherein said non-cutting tip comprises a conical tip.

8. The successive set of endodontic instruments of claim 7, wherein said conical tip comprises a 60 degree taper angle.

9. The successive set of endodontic instruments of claim 1, wherein at least one of said cutting surfaces comprises a nickel-titanium alloy.

10. The successive set of endodontic instruments of claim 1, wherein at least one of said cutting surfaces comprises radial lands.

11. The successive set of endodontic instruments of claim 1, wherein at least one of said cutting surfaces comprises between about 1.5 mm and 10.0 mm in length.

12. The successive set of endodontic instruments of claim 1, wherein said cutting surfaces have a taper between about 0.067 mm/mm and about 0.133 mm/mm.

13. The successive set of endodontic instruments of claim 1, wherein said succeeding cutting surface has a different taper than said preceding cutting surface.

14. A set of endodontic instruments for preparing a root canal, comprising:
   a plurality of files, each of said files having a tapered cutting portion defined by a maximum diameter and a minimum diameter, and wherein said minimum diameter of a first of said files substantially equals said maximum diameter of a second of said files.

15. The set of endodontic instruments of claim 14, wherein said plurality of succeeding tapered files are equally tapered.

16. The set of endodontic instruments of claim 15, wherein said plurality of succeeding tapered files consists of a first file, a second file, and a third file.

17. The set of endodontic instruments of claim 16, wherein said minimum diameter of said first file comprises about 0.25 mm and said maximum diameter of said first file comprises about 0.45 mm.

18. The set of endodontic instruments of claim 16, wherein said minimum diameter of said second file comprises about 0.45 mm and said maximum diameter of said second file comprises about 0.65 mm.

19. The set of endodontic instruments of claim 16, wherein said third file comprises a minimum diameter of about 0.65 mm.

20. The set of endodontic instruments of claim 16, wherein said cutting portion is between about 1 mm and about 10 mm in length.

21. The set of endodontic instruments of claim 14, wherein said minimum diameter of a third of said files substantially equals said maximum diameter of said second of said files.

22. The set of endodontic instruments of claim 14, wherein each of said plurality of files has a non-cutting tip adjacent said tapered cutting portion.

23. The set of endodontic instruments of claim 22, wherein each of said non-cutting tips has a substantially equal diameter.

24. A set of endodontic instruments for preparing a root canal, comprising:
   a first tapered file having a first minimum diameter and a first maximum diameter, said first file having a taper ratio greater than about 0.06 mm/mm; and
   a second tapered file having a second minimum diameter and a second maximum diameter, said second minimum diameter being substantially equal to said first maximum diameter.

25. The set of endodontic instruments of claim 24, further comprising:
   a third tapered file having a third minimum diameter and a third maximum diameter, said third minimum diameter being substantially equal to said second maximum diameter.

26. The set of endodontic instruments of claim 25, wherein said third tapered file has a taper ratio greater than about 0.06 mm/mm.

27. The set of endodontic instruments of claim 24, wherein said second tapered file has a taper ratio greater than about 0.06 mm/mm.

28. A method of preparing a root canal for filling, comprising:
   firstly filing to a cementodentinal junction of said root canal using a first instrument having a taper ratio greater than about 0.06 mm/mm;
   secondly filing to a first point proximal of said cementodentinal junction using a second instrument having a taper ratio greater than about 0.06 mm/mm and having a minimum diameter substantially equal to a maximum diameter of said first instrument; and
   thirdly filing to a second point proximal of said first point using a third instrument having a taper ratio greater than about 0.06 mm/mm.

29. The method of claim 28 wherein said first instrument, said second instrument, and said third instrument comprise substantially the same taper.

30. The method of claim 28 wherein said first instrument, said second instrument, and said third instrument comprise different tapers.

31. The method of claim 28, wherein a minimum diameter of said third instrument substantially equals a maximum diameter of said second instrument.

* * * * *